(12) United States Patent
Rapoport

(10) Patent No.: US 9,072,644 B2
(45) Date of Patent: Jul. 7, 2015

(54) PREMATURE NEONATE CLOSED LIFE SUPPORT SYSTEM

(75) Inventor: Uri Rapoport, Moshav Ben Shemen (IL)

(73) Assignee: ASPECT IMAGING LTD, Shoham (IL)

(*) Notice: Subject to any disclaimer, the term of this patent is extended or adjusted under 35 U.S.C. 154(b) by 345 days.

(21) Appl. No.: 13/595,195

(22) Filed: Aug. 27, 2012

(65) Prior Publication Data
US 2013/0267765 A1 Oct. 10, 2013

(30) Foreign Application Priority Data

Apr. 4, 2012 (DE) ...................... 20 2012 101 227 U

(51) Int. Cl.
A61G 11/00 (2006.01)
A61G 10/00 (2006.01)
A61B 5/055 (2006.01)

(52) U.S. Cl.
CPC ............ A61G 11/005 (2013.01); A61G 10/005 (2013.01); A61G 11/00 (2013.01); A61B 5/0555 (2013.01); A61B 2503/045 (2013.01); A61G 2210/50 (2013.01); A61G 11/009 (2013.01); A61G 2203/46 (2013.01)

(58) Field of Classification Search
CPC ... A61G 11/00; A61G 11/001; A61G 11/002; A61G 11/003; A61G 11/004; A61G 11/005; A61G 11/006; A61G 11/007; A61G 11/008; A61G 11/009; A61G 10/02

USPC .......................................... 600/21–22; 5/655
See application file for complete search history.

(56) References Cited

U.S. PATENT DOCUMENTS

| | | | |
|---|---|---|---|
| 3,710,791 A * | 1/1973 | Deaton ..................... | 128/205.26 |
| 5,759,149 A * | 6/1998 | Goldberg et al. ................ | 600/22 |
| 7,255,671 B2 * | 8/2007 | Boone et al. ..................... | 600/22 |
| 2011/0172487 A1 * | 7/2011 | Khodak et al. .................. | 600/22 |

OTHER PUBLICATIONS

International Electrotechnical Commission, IEC 60601-2-19 Medical Electrical Equipment—Part 2-19: Particular requirements for the basic safety and essential performance of infant incubators. 2009.*

* cited by examiner

Primary Examiner — Charles A Marmor, II
Assistant Examiner — Carrie R Dorna
(74) Attorney, Agent, or Firm — The Law Office of Michael Kondoudis

(57) ABSTRACT

A magnetically permeable neonate transport capsule (MPNTC) for transporting a premature neonate from a host infant incubator having a steady environmental condition to an MRD. The MPNTC has at least one first normally open configuration when the capsule is disposed within the incubator and a second closed configuration for removal, transportation, insertion, measurement and vice versa within an MRD device. The MPNTC includes an environmental control system thereby adapted to maintain continuous attachment of the neonate with life support connection lines. The MPNTC is further adapted to maintain environmental conditions substantially similar to the host infant incubator environmental condition when the MPNTC is transported from the incubator to the MRD device.

7 Claims, 3 Drawing Sheets

PREMATURE NEONATE CLOSED LIFE SUPPORT SYSTEM

FIELD OF THE INVENTION

The present invention generally pertains to an improved premature neonate closed life support system for use in medical devices, especially a portable MRD device

BACKGROUND OF THE INVENTION

Neonates are typically accommodated in incubators in a dedicated premature baby ward or department of a hospital. The incubators are typically not robust and the general health of the neonate is often compromised. Each disturbance or perturbation of the neonate can have deleterious consequences. Nevertheless it is often essential to transfer the neonate to MRI devices and rooms located at a distance from the premature baby ward. This entails disconnecting the neonate from life supporting connection lines and systems and then reconnecting the life supporting connection lines and systems. Such activities may be dangerous to the neonate patients.

Prior art systems provide a solution for transferring a neonate from an incubator to the MRI device. Providing devices and methods for transferring a neonate, whilst avoiding dangerous exposure of the neonate to the external environment and without endangering the neonate by disconnection of the life supporting connection lines, would fulfill a long felt need.

SUMMARY OF THE INVENTION

It is thus an object of the invention to disclose a novel magnetically permeable neonate transport capsule (MPNTC) for transporting a premature neonate from a host infant incubator having a steady environmental condition to an MRD. The MPNTC having at least one first normally open configuration when the capsule is disposed within said incubator and a second closed configuration for removal, transportation, insertion, measurement and vice versa within an MRD device. MPNTC is preferably, yet not exclusively made by various methods and means, such as a set of transformable CLNS, as shown in figures below; a capsule characterized in at least one portion, by a kit of inflatable-side walls and top ceiling members; a capsule characterized in at least one portion, by a collapsible skeleton; a capsule characterized in at least one portion, by an articulated skeleton etc. The MPNTC comprises an environmental control system thereby adapted to maintain continuous attachment of the neonate with life support connection lines. The MPNTC is further adapted to maintain environmental conditions substantially similar to the host infant incubator environmental condition when the MPNTC is transported from the incubator to the MRD device. The environmental control system is selected from the group consisting inter alia heat insulation means, an operative connection to a temperature regulation system, an operative connection to a humidity regulation system, an operative connection to an air supply system, an operative connection to an oxygen regulation system, an operative connection to a $CO_2$ regulation system. MPNTC's environmental control system, by being adapted to maintain the environmental conditions substantially similar to the host infant incubator environmental condition when the MPNTC is transported from the incubator to said MRD device, meets at least one member of a group of standards consisting of IEC 6061-2-19 Standard Clauses 12 201.12.101 (Stability of incubator); IEC 201.12.102 (Uniformity of incubator temperature); IEC 201.12.103 (Accuracy of skin temperature sensor); IEC 201.12.1.104 (accuracy between skin temperature and control temperature during removal, transportation and insertion within said MRD device); IEC 201.12.1.108 (overshoot time) and/or IEC 12 201.12.1.107 (warm up time).

BRIEF DESCRIPTION OF THE DRAWINGS

The present invention will be more readily understood from the detailed description of embodiments thereof made in conjunction with the accompanying drawings of which.

DETAILED DESCRIPTION OF THE PREFERRED EMBODIMENTS

Figure 1:
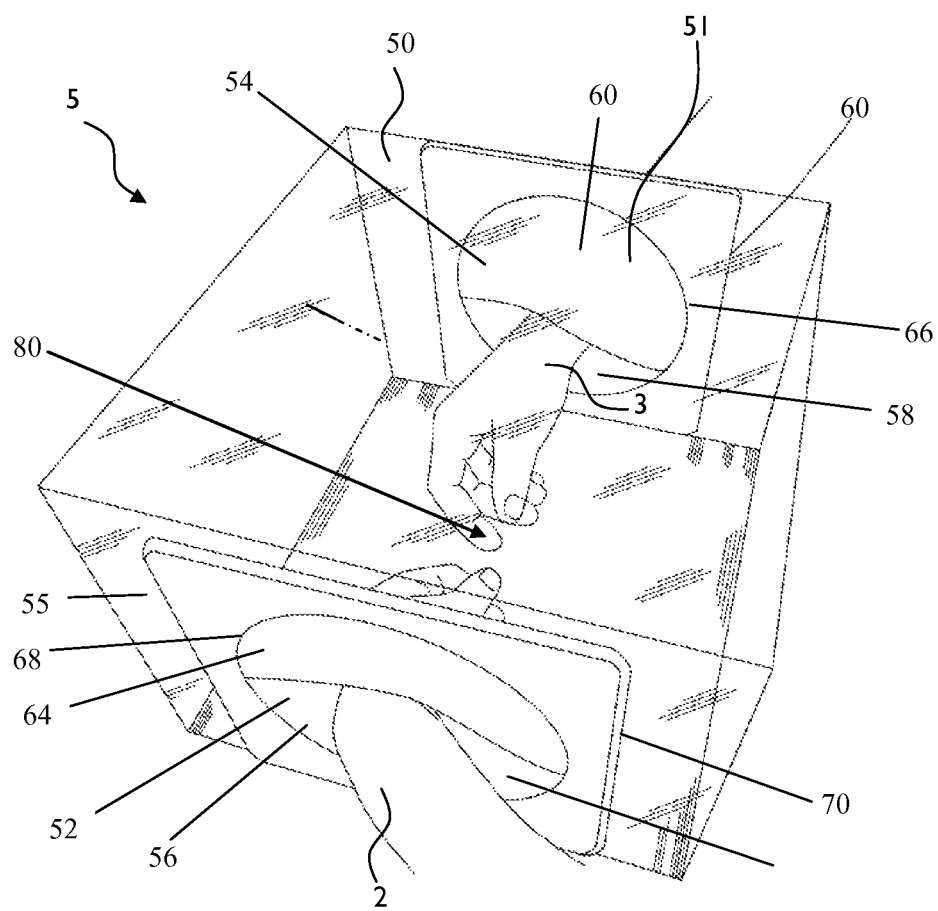
FIG. 1 is a schematic illustration of a neonate incubator.

The following description is provided, alongside all chapters of the present invention, to enable any person skilled in the art to make use of the invention and sets forth the best modes contemplated by the inventor of carrying out this invention. Various modifications, however, will remain apparent to those skilled in the art, since the generic principles of the present invention have been defined specifically to provide a premature neonate closed life support system and methods thereof.

The term 'magnetic resonance device' (MRD) specifically applies hereinafter to any Magnetic Resonance Imaging (MRI) device, any Nuclear Magnetic Resonance (NMR) spectroscope, any Electron Spin Resonance (ESR) spectroscope, any Nuclear Quadruple Resonance (NQR) or any combination thereof. The term, in this invention, also applies to any other analyzing and imaging instruments comprising a volume of interest, such as computerized tomography (CT), ultrasound (US) etc. The MRD hereby disclosed is optionally a portable MRI device, such as the ASPECT-MR Ltd commercially available devices, or a commercially available non-portable device. Moreover, the term 'MRD' interchangeably refers in general to any non-incubator medical devices, at least temporary accommodating the neonate.

As used herein, the term "neonate" generally refers to any object or living creature, such as human being or other mammal and preferably refers to babies.

As used herein, the term "incubator" may include isolate-like devices which are a self-contained incubator units that provides a controlled heat, humidity, and oxygen microenvironment for the isolation and care of premature and low-birth weight neonates. The apparatus is often made of a clear plastic material and has a large door and portholes for easy access to the infant with a minimum of heat and oxygen loss. A servo control mechanism constantly monitors the infant's temperature and controls the heat within the unit.

As used herein the term "host incubator" refers to the incubator in which the infant resides and from which the magnetically permeable neonate transport capsule described herein is removed.

As used herein, the term "plurality" refers in a non-limiting manner to any integer equal or greater than 1.

The term 'about' refers herein to a value of ±25% of the defined measure.

The term "A magnetically permeable neonate transport capsule" or "capsule" refers herein to a means such as a cradle-like neonate support (CLNS) having suitable dimensions and geometric-configuration for accommodating at least one premature neonate. Such a CLNS has at least two operational configurations, said operational configurations comprising: a first operational OPEN configuration whereby said CLNS is adapted to couple said neonate to at least one life supporting system by means of at least one life supporting coupling line, prior to positioning said CLNS in a medical device, and a second operational air-tight CLOSED configuration whereby said neonate remains continuously coupled to said at least one life supporting system by means of at least one life supporting coupling line, when positioning said CLNS within said medical device, wherein said OPEN and CLOSED configurations are reversible. This CLNS or capsule or magnetically permeable neonate transport capsule is provided to be the means of transport from the infant incubator to the MRD device and back to the incubator.

It is acknowledged in this respect that according to the present invention, the said NCLSS is provided by any suitable manner, which may include, in a non limiting manner, a set of transformable or rotatable CLNS, as shown in figures below; a capsule characterized in at least one of its portions, by a plurality of inflatable/deflatable-side walls and/or top ceiling members; a capsule characterized in at least one of its portions, by a collapsible skeleton; a capsule characterized in at least one of its portion, by an articulated skeleton or any combination thereof.

Reference is now made to FIG. 1, schematically illustrating in a not to scale manner a neonate's incubator. More specifically, an incubator 5 presented in FIG. 1 is provided, rendered useful by means of size, shape and dimensions to at least temporarily accommodate in its inner air tight sealed volume 53 a neonate under medical care, e.g., anesthetics, imaging or other diagnostics or treatment. The incubator 5 comprises, inter alia, operator hand access ports, 51 and 52, for operator hands 3 and 2, respectively. Each one of the ports 51 and 52 comprises a port aperture 54 and 56, located on incubator walls 50 and 55, respectively, and at least two pairs of flexible non-resilient lightweight sealing gas-tight flaps (SFs) (58 and 60) and (62 and 64), disposed within the same plane of the port apertures 54 and 56, respectively, in an overlapping manner, thereby entirely enclosing the respective port apertures 54 and 56. Each pair of the SFs (58 and 60) and (62 and 64) is attached to port aperture edges 66 and 68, respectively and incubator supporting flanges 68 and 70, respectively. The incubator flanges 66 and 68 are attached to the incubator walls 50 and 5355 and each member of the pair of flaps (58 and 60) and (62 and 64) are in an overlapping arrangement, as shown in FIG. 1. The members of each pair of flaps (58 and 60) and (62 and 64) are stretched across each respective port aperture 54 and 56 thereby enclosing and defining an interior access zone 80, disposed within the same plane of the port aperture and characterized solely by the port flanges 66 and 68 of each pair of SFs (58 and 60) and (62 and 64).

Figure 2:
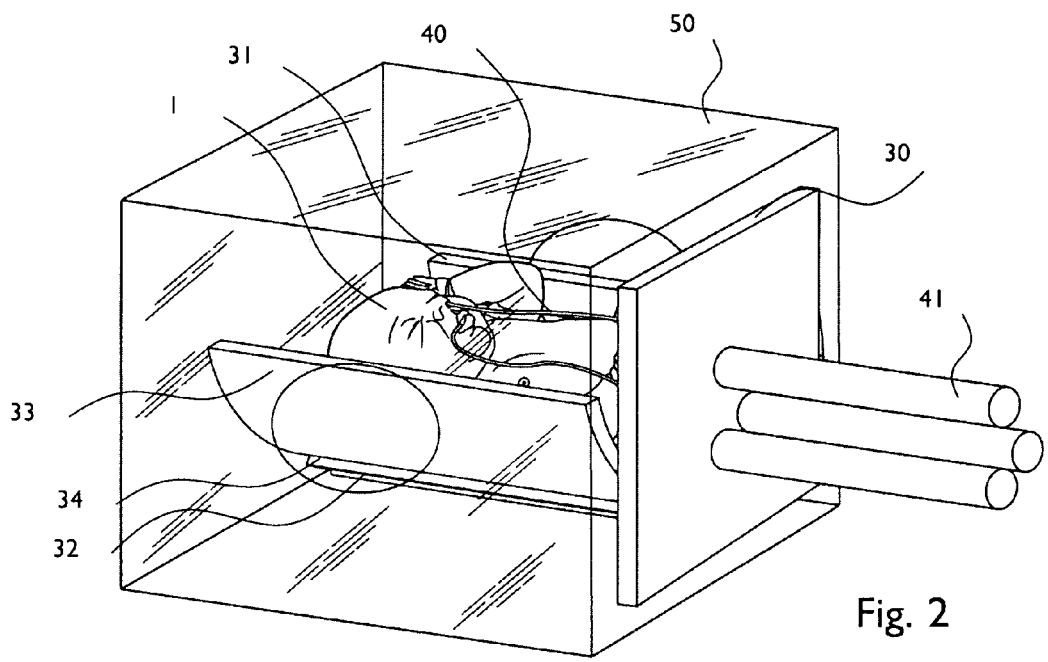
FIG. 2 is a schematic illustration of a neonate incubator in which a premature neonate closed life support system (NCLSS) is located within the inner volume of the incubator.

Reference is now made to FIG. 2, schematically illustrating in a not to scale manner the neonate's incubator 50, wherein the premature neonate closed life support system (NCLSS) is located within the inner volume of the incubator 50. The NCLSS system comprises, inter alia, at least one chamber comprising a cradle-like neonate support (32) sized and shaped for accommodating at least one premature neonate 1. CLNS is reversibly transformable from an OPEN configuration, as presented in FIG. 2, in which the CLNS is adapted to couple the neonate with at least one life supporting connection line, prior to insertion into a medical device, such as an MRD; to an air tight CLOSED configuration as presented in FIG. 3, in which the chamber is permeable to magnetic fields and suitable to be set within said MRD device. This open/close configuration is achievable in various mechanisms, such as rotating, advancing, reciprocating, transversing, or otherwise maneuvering pre-shaped flaps, inflating/deflating skeletoned or non-skeletoned side walls and/or ceiling by fluids such as gas (e.g., compressed air), and/or liquids (e.g., cooled/warmed pumped water), collapsing either skeletoned or non-skeletoned structure, erecting articulated either skeletoned or non-skeletoned structure etc.

According to one embodiment of the invention, and in a non-limiting manner, the CLNS is constructed by a plurality of maneuverable flaps, flaps 31-34, wherein in the OPEN configuration; upper flap 33 has a curved cradle-like shape. The neonate 1 is conveniently and safely positioned on top of flap 33. Other curved flaps, namely 32-34, slide beneath flap 31. The CLNS further comprises side wall 30 which is adapted to fit wall 52 as presented in FIG. 1, which is the planar support for communicating a plurality of at least one life supporting connection lines positioned within the incubator, namely lines 40, with those positioned outside the incubator (41). The neonate 1 thus is maintained and treated within incubator 50 or in any commercially available incubator.

Figure 3:
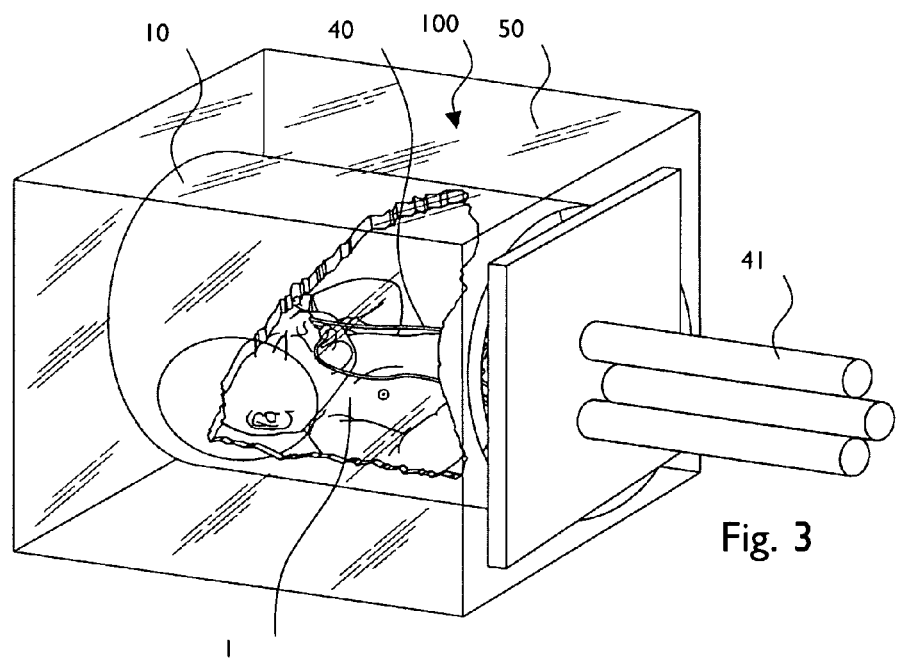
FIG. 3 is a schematic illustration of a neonate incubator in which all flaps are closed to form air tight capsule.

Reference is now made to FIG. 3, schematically illustrating in an out-of-scale manner neonate's incubator 50, wherein all flaps are closed to form air tight capsule 100 in the CLOSE configuration. Neonate 1 is enveloped within capsule 100 having a continuous wall or envelope 10, such that the internal life supporting connection lines 40 are in communication with the external life supporting connection lines 41.

Figure 4:
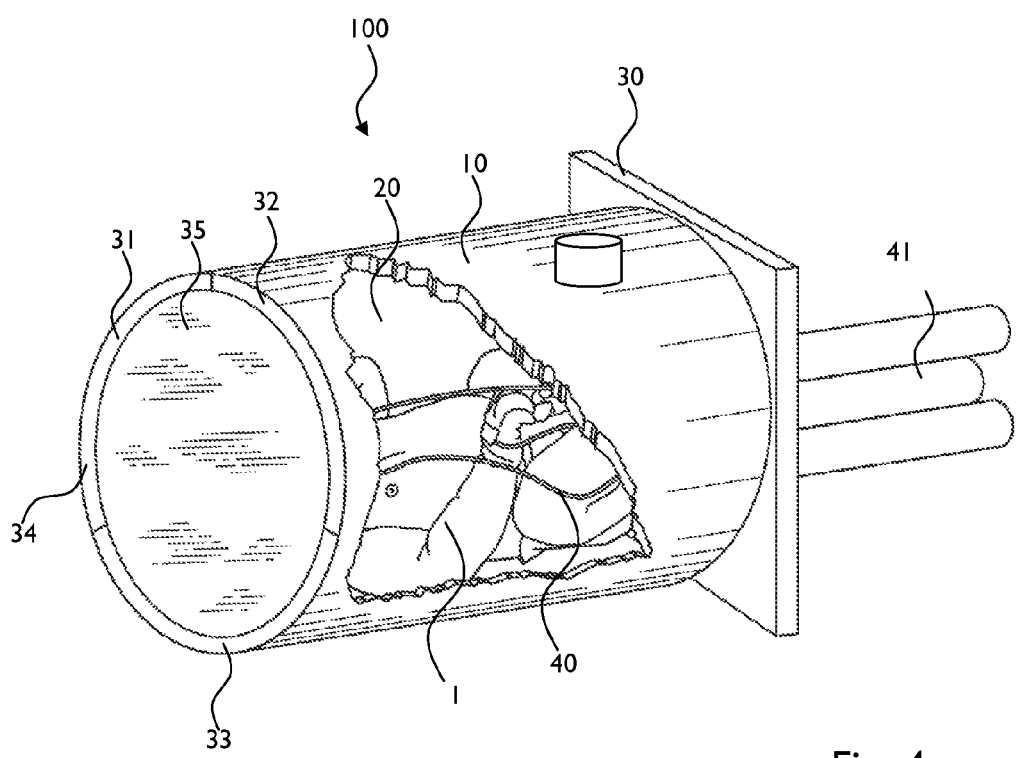
FIG. 4. is a schematical illustration of a portable cradle-like neonate support (CLNS).

Reference is now made to FIG. 4, schematically illustrating in an out of scale manner portable CLNS 100. According to the embodiment described above, the walls of air tight capsule 100 comprise a shell 10 constructed by four curved flaps 31-34, side walls 30 and 35. The encapsulated environment, i.e., confined volume 20 within the capsule is separated from the outside by shell 10, such that all life supporting connection lines 40 within the capsule are connected to the same outer life supporting connection lines 41. In this manner, transformation of chamber 10 from its OPEN configuration to its air tight CLOSED configuration is provided while the neonate 1 is continuously maintained connected to the at least one life supporting connection line. Dangerous exposure of the neonate to external environment is avoided. Endangering the patient by disconnection of the life supporting connection lines 40 is overcome.

It is herein acknowledged that the heat insulation means, and various operative connections to the temperature regulation system, a humidity regulation system, air supply system, oxygen regulation system, $CO_2$ regulation system and other operative connections are conventional and available to a person skilled in the art as described herein.

The core of the invention is a magnetically permeable neonate transport capsule (MPNTC) for transporting a premature neonate from an host infant incubator having a steady environmental condition to an MRD device, said MPNTC having a first normally open configuration when said capsule is disposed within said incubator and a second closed configuration for removal, transportation, insertion, measurement and vice versa within an MRD device wherein said MPNTC comprises an environmental control system said MPNTC adapted to maintain continuous attachment of said neonate with life support connection lines, further wherein said MPNTC is adapted to maintain environmental conditions substantially similar to said host infant incubator environmental condition when said MPNTC is transported from said incubator to said MRD device; said environmental control system is selected from the group consisting of 10 heat insulation means, 41 an operative connection to a temperature regulation system, an operative connection to a humidity regulation system, an operative connection to an air supply system, an operative connection to an oxygen regulation system, an operative connection to a $CO_2$ regulation system; wherein said MPNTC's environmental control system meets at least one member of a group of standards consisting of IEC 6061-2-19 Standard Clauses 12 201.12.101 (Stability of incubator); IEC 201.12.102 (Uniformity of incubator temperature); IEC 201.12.103 (Accuracy of skin temperature sensor); IEC 201.12.1.104 (accuracy between skin temperature and control temperature during removal, transportation and insertion within said MRD device); IEC 201.12.1.108 (overshoot time) and/or IEC 12 201.12.1.107 (warm up time).

According to an embodiment of the invention, the MPNTC describe above is provided useful for transporting a premature neonate from a host infant incubator, wherein said MPNTC comprises at least one environmental sensing and alarm system.

According to an embodiment of the invention, the MPNTC describe above is provided useful wherein said at least one environmental sensing and alarm system comprises feedback control.

According to an embodiment of the invention, the MPNTC describe above is provided useful the said environmental sensing and alarm system is selected from the group consisting of a temperature alarm humidity alarm, air supply alarm, oxygen concentration alarm, $CO_2$ concentration alarm.

According to an embodiment of the invention, the MPNTC describe above is provided useful wherein it is adapted to maintain temperature conditions substantially similar to said host infant incubator temperature conditions wherein said capsule has a steady temperature condition within a range of about +/−0.5 degrees Celsius of said incubator when said capsule is transported from said incubator to said MRD device.

According to an embodiment of the invention, the MPNTC describe above is provided useful wherein said predetermined steady temperature condition is maintained over a period of at least one hour when checked at about 32 degrees Celsius and about 36 degrees Celsius.

According to an embodiment of the invention, the MPNTC describe above is provided useful wherein said MPNTC is adapted to maintain similar temperature conditions to said baby controlled incubator namely said predetermined steady temperature condition during baby control mode are maintained such that the skin temperature of the neonate does not differ from said predetermined steady temperature condition by more than 0.7 degrees Celsius.

According to an embodiment of the invention, the MPNTC describe above is provided useful wherein it is adapted to maintain similar conditions to said incubator namely that when the control temperature of said incubator is set at 12 degrees Celsius above ambient temperature, supply voltage being equal to the rated voltage, said incubator operating as an air controlled infant incubator, said infant incubator is switched on starting from cold condition, and time for the incubator temperature to rise by 11 degrees Celsius is measured, the warm up time of said capsule substantially conforms with warm up time of said incubator.

According to an embodiment of the invention, the MPNTC describe above is provided useful wherein said capsule is adapted to maintain an overshoot temperature of 2 degrees Celsius temperature within said incubator.

According to an embodiment of the invention, the MPNTC describe above is provided useful wherein said capsule is adapted to maintain said temperature during a 15 minute steady state temperature condition restoration period.

According to yet another embodiment of the invention, the MPNTC describe above is provided useful to maintain substantially similar temperature conditions to that of said incubator when said infant incubator is operated as an air controlled incubator at a control temperature of 32 degrees until said steady state temperature is reached, and the temperature is then adjusted to a control temperature of 36 degrees Celsius, the overshoot of incubator and the time to reach the new steady temperature condition from the first passage of 36 degrees Celsius being measured.

The invention claimed is:

1. A magnetically permeable neonate transport capsule (MPNTC) for transporting a premature neonate from a host infant incubator having a steady environmental condition to a magnetic resonance device (MRD); said MPNTC is adapted to maintain an environmental condition substantially similar to said steady environmental condition of said host infant incubator when transported from said host infant incubator to said MRD; said MPNTC comprises:

a cradle-like support dimensioned to accommodate said premature neonate and a set of maneuverable members integrated with said support and configured to reversibly form together with said support an air tight capsule when maneuvered to a closed position, such that said MPNTC is reversibly transformable from an open configuration to a closed configuration when disposed within said host infant incubator, with no need to open said host infant incubator, said maneuverable members comprising a plurality of curved flaps reversibly slidable beneath said cradle-like support; and an environmental control system adapted to maintain continuous attachment of said MPNTC to life support connection lines; said life support connection lines is are selected from the group consisting of heat insulation means, an operative connection to a temperature regulation system, an operative connection to a humidity regulation system, an operative connection to an air supply system, an operative connection to an oxygen regulation system, an operative connection to a $CO_2$ regulation system;

wherein said MPNTC's environmental control system, by being adapted to maintain said environmental conditions substantially similar to said host infant incubator environmental condition when said MPNTC is transported from said incubator to said MRD, meets at least one member of a group of International Electrotechnical Commission (IEC) standards consisting of IEC 6061-2-19 Standard Clauses 12 201.12.101 (Stability of incubator); IEC 201.12.102 (Uniformity of incubator temperature); IEC 201.12.103 (Accuracy of skin temperature sensor); IEC 201.12.1.104 (accuracy between skin temperature and control temperature during removal, transportation and insertion within said MRD device); IEC 201.12.1.108 (overshoot time) and/or IEC 12 201.12.1.107 (warm up time).

2. The magnetically permeable neonate transport capsule according to claim 1 wherein said MPNTC comprises at least one environmental sensing and alarm system.

3. The magnetically permeable neonate transport capsule according to claim 2 wherein said at least one environmental sensing and alarm system comprises a feedback control.

4. The magnetically permeable neonate transport capsule according to claim 3 wherein said environmental sensing and alarm system is selected from the group consisting of a temperature alarm, humidity alarm, air supply alarm, oxygen concentration alarm, $CO_2$ concentration alarm.

5. The magnetically permeable neonate transport capsule according to claim 2 wherein said environmental sensing and alarm system is selected from the group consisting of a temperature alarm humidity, alarm, air supply alarm, oxygen concentration alarm, $CO_2$ concentration alarm.

6. The magnetically permeable neonate transport capsule according to claim 1, wherein said capsule has a steady temperature condition within a range of about +/−0.5 degrees Celsius of the temperature in said host infant incubator when said capsule is transported from said host infant incubator to said MRD device.

7. The magnetically permeable neonate transport capsule according to claim 6 wherein said steady temperature condition is maintained over a period of at least one hour.

\* \* \* \* \*